US008617091B2

(12) United States Patent
Brannon et al.

(10) Patent No.: US 8,617,091 B2
(45) Date of Patent: Dec. 31, 2013

(54) ANIMAL SPINE BRACE

(76) Inventors: Cory Michael Brannon, Spokane, WA (US); Veronica Claire Brannon, Spokane, WA (US)

( * ) Notice: Subject to any disclaimer, the term of this patent is extended or adjusted under 35 U.S.C. 154(b) by 43 days.

(21) Appl. No.: 13/324,553

(22) Filed: Dec. 13, 2011

(65) Prior Publication Data

US 2012/0316484 A1 Dec. 13, 2012

Related U.S. Application Data

(60) Provisional application No. 61/462,745, filed on Feb. 8, 2011.

(51) Int. Cl.
*A61F 5/00* (2006.01)

(52) U.S. Cl.
USPC .............................................. 602/19; 119/850

(58) Field of Classification Search
USPC ............... 602/18, 19; 128/874–875; 119/809, 119/814, 815, 850, 856
See application file for complete search history.

(56) References Cited

U.S. PATENT DOCUMENTS

D110,625 S 7/1938 Nesbitt
2,831,306 A 4/1958 Brenton
4,385,592 A * 5/1983 Goldstein ........................ 602/18
4,715,618 A 12/1987 Harris
D313,291 S 12/1990 Shanley
D313,676 S 1/1991 Indursky et al.
5,137,508 A * 8/1992 Engman ........................... 602/79
D407,865 S 4/1999 Rylander
6,123,049 A 9/2000 Slater
6,138,611 A 10/2000 Thielemann
6,267,083 B1 * 7/2001 Chimienti ..................... 119/850
D453,594 S 2/2002 Ishihara
D459,842 S 7/2002 Kaplan
6,443,101 B1 9/2002 Fazio
6,481,383 B1 * 11/2002 Ross et al. .................... 119/850
D479,896 S 9/2003 Wilson
6,662,754 B1 12/2003 Wilson
D584,862 S 1/2009 Kemper
7,665,425 B2 2/2010 Gross
D633,257 S 2/2011 Trias
D651,364 S 12/2011 Luckenbach
2003/0177984 A1 9/2003 Newman
2005/0229869 A1 10/2005 Leo
2006/0156997 A1 7/2006 Moore
2008/0134991 A1 6/2008 DePass
2010/0199507 A1 8/2010 Gonzalez et al.

OTHER PUBLICATIONS

"Wiggle Less (TM) Prevention and Back Support for Dogs with Back Problems", *Design Information;* retrieved from http://www.wiggle-less.com/design/ on Jan. 20, 2012, 3 pages.

* cited by examiner

*Primary Examiner* — Michael A. Brown
(74) *Attorney, Agent, or Firm* — Wolfe-SBMC

(57) ABSTRACT

An animal spine brace is described. In one or more implementations, a brace is comprised of an upper panel and a lower panel that extends from the upper panel. The lower panel is configured to be releasably secured to the upper panel to form a sleeve around an animal. The upper and lower panels may be made of a breathable material that is configured to stretch, wick moisture from the animal, and/or control odor. Additionally, both the upper panel and lower panel are configured to include supportive stays, which may be arranged on a respective panel to fan out.

20 Claims, 4 Drawing Sheets

ANIMAL SPINE BRACE

RELATED APPLICATION

This application claims priority to U.S. Provisional Application Ser. No. 61/462,745 filed Feb. 8, 2011, entitled "Orthopedic Breathable Canine Brace" to Cory M. Brannon et al., the disclosure of which is hereby incorporated by reference in its entirety.

BACKGROUND

An animal's spine is formed from vertebrae (bones), which are connected by flexible cartilage discs. These discs, which are also called "intervertebral discs," act as cushions between each vertebra and allow for movement of the neck, spine, and tail.

In some cases, these discs may become weak and can rupture or herniate. This can cause the disc to protrude causing a painful condition for the animal. For animals suffering from this condition, veterinarians conventionally ordered several weeks of crate rest as well as suggested restrictions to the activity of the animal, e.g., no stairs, no jumping, and mild to limited exercise. Sadly, an estimated one in five dogs will suffer from this condition, which often causes intense pain and may even lead to paralysis.

SUMMARY

An animal spine brace is described. In one or more implementations, a brace is comprised of an upper panel and a lower panel that extends from the upper panel. The lower panel is configured to be releasably secured to the upper panel to form a sleeve around an animal. Additionally, adjustable loops that wrap around front and rear legs of the animal may be formed by straps that extend from the upper and lower panels.

In one or more implementations, the upper and lower panels may be made, for example, of a breathable material that is configured to stretch. The material may also be configured to wick moisture from the animal, and/or control odor.

In one or more implementations, the upper and lower panels are configured to wrap around an animal to form an adjustable sleeve and include multiple supportive stays. A material that is substantially rigid may be used to make the supportive stays. When the brace is wrapped around the animal, supportive stays integrated with the upper panel are configured to "fan out" across the upper sides and back of the animal. The lower panel may also include multiple supportive stays. These supportive stays may also be configured to "fan out" across the chest and abdomen of the animal when the brace is wrapped around the animal.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items. Entities represented in the figures may be indicative of one or more entities and thus reference may be made interchangeably to single or plural forms of the entities in the discussion.

DETAILED DESCRIPTION

Overview

Figure 1:
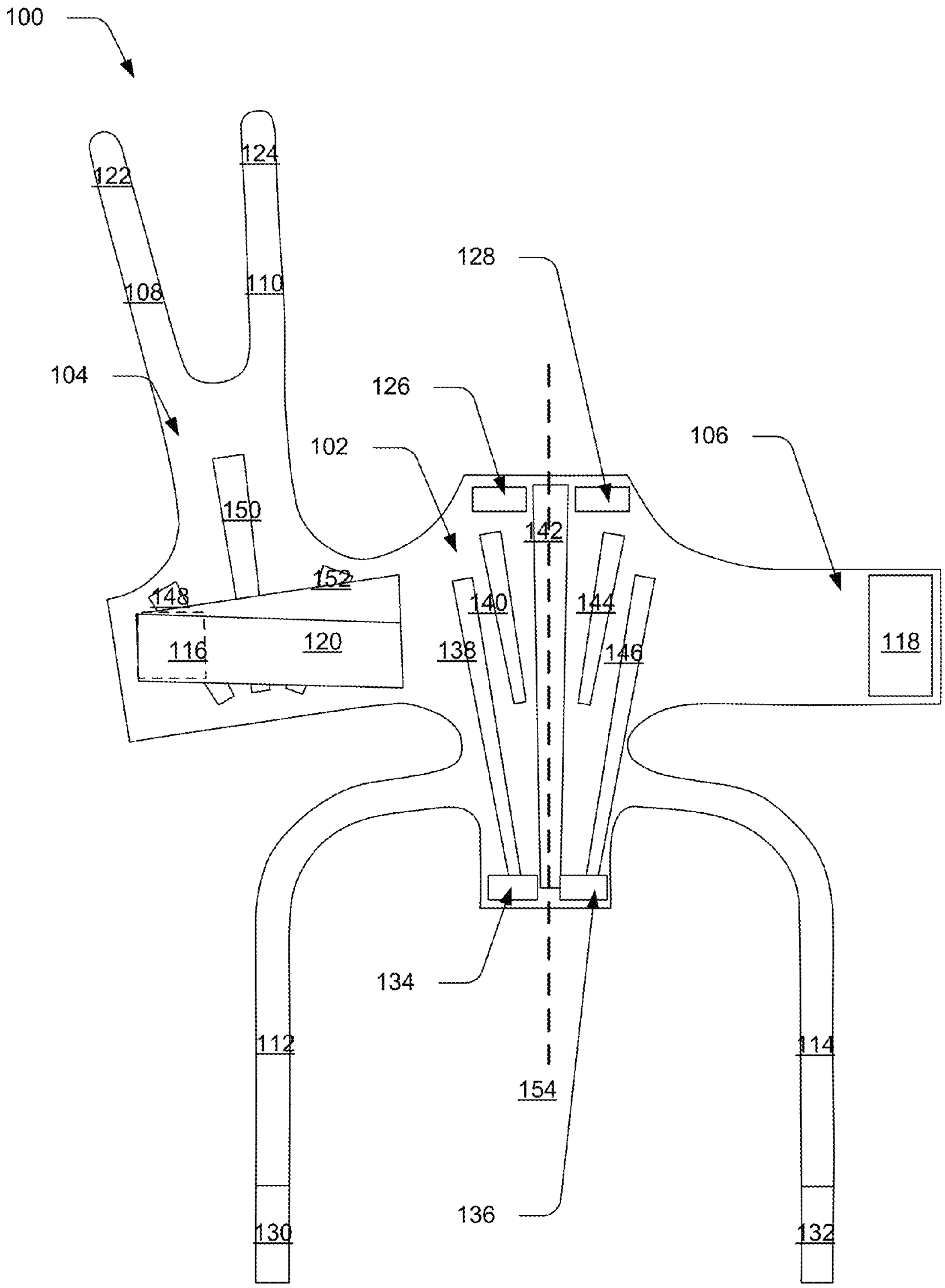
FIG. 1 is an illustration of a brace in an example implementation that is configured to form an adjustable sleeve around an animal.

An animal's spine is formed from vertebrae, which are connected by flexible cartilage discs. These discs are called "intervertebral discs" and act as cushions between the vertebrae and allow for movement of the animal's neck, spine, and tail. In some cases, these discs may become weak and can rupture or herniate. This can cause the disc to protrude, a very painful condition for the animal. This condition is known as Intervertebral Disk Disease (IVDD).

Back problems are not uncommon for dogs. In particular, IVDD is often seen in small dog breeds such as Dachshunds, Pekingese, Beagles, Corgi, Shih Tzu, and other similar breeds which tend to have relatively shorter legs and longer bodies. IVDD is especially prevalent among Dachshunds. However, it should be noted that this ailment may occur with any type of animal, not just the small breeds of dog mentioned above.

IVDD is a serious condition that may result in intense pain and can sometimes result in paralysis. Dogs suffering from IVDD often demonstrate signs of severe discomfort, such as whimpering, shivering, or shaking, dragging of the rear legs and in some cases loss of bladder or bowel control. Normally, a veterinarian will order several weeks of crate rest, no stairs, no jumping and mild to limited exercise for a dog suffering from IVDD. Conventional approaches to brace construction have done little to alleviate the discomfort experienced by these dogs (and thus the resulting misery experienced by the dogs' owners). For example, traditional braces were often difficult for an owner to put on a dog and/or were often constructed of material that was uncomfortable when worn by the dog.

An animal spine brace is described that helps keep an animal's back and abdomen supported and in place, so that a weakened and ruptured or herniated disc will not worsen. For example, the animal spine brace may be wrapped around the midsection of a dog to keep the dog from aggravating a back problem, such as a back problem associated with IVDD. Specifically, the animal spine brace helps to alleviate pressure on an animal's back that results from a ruptured or herniated disc by stabilizing the animal's back. This in turn minimizes the pain for the animal. The animal spine brace can also aid in the post-operative healing process (e.g., from an operation to correct a ruptured or herniated disc). The animal spine brace may be used on an animal even after a protruding disc heals, such as on a dog that has already suffered from a protruding disc, as dogs prone to these injuries have a high probability of reoccurrence.

In one or more implementations, the animal spine brace has an "open" design making the brace easy to put on and take off. Using a series of releasable closures, for instance, the animal spine brace may be easily secured around an animal. In one example, adjustable straps may be used to form loops that support the shoulders and legs of the animal. To provide further comfort for the animal, the brace may be constructed from a breathable lightweight material.

In the following discussion, a brace is described by way of example as being worn by a dog having a back problem and/or having a propensity for back problems. However, it should be readily apparent that the following discussion is not limited to a dog, or to an animal having back problems or a propensity for them. Accordingly, a brace used on variety of different animals (e.g., other domestic animals, livestock, animals at the zoo, wild animals, those without back problems, and so on) may employ the techniques described herein without departing from the spirit and scope thereof.

Example Brace

FIG. 1 is an illustration of brace 100 in an example implementation that is configured to form an adjustable sleeve around an animal. The illustrated brace 100 includes an upper panel 102 and a lower panel 104 that extends from the upper panel 102. The lower panel 104 extends from the upper panel 102 such that when the brace 100 is wrapped around an animal, it forms a sleeve around the animal. For example, when the brace 100 is wrapped around an animal, upper panel 102 covers upper side and back portions of the animal and the lower panel 104 covers lower side, abdomen, and chest portions of the animal. As illustrated, the lower panel 104 extends from a portion of the upper panel 102 that corresponds to a side of an animal when brace 100 is worn. In this example, the upper panel 102 includes an abdominal securing strap 106. The abdominal securing strap 106 extends from a portion of the upper panel 102 directly across the upper panel from where the lower panel 104 extends. Thus, the portion of the upper panel 102 from which the abdominal securing strap 106 extends corresponds to an opposite side of the animal when brace 100 is worn.

In the illustrated example, brace 100 includes front leg straps 108, 110 that extend from the lower panel 104, and rear leg straps 112, 114 that extend from the upper panel 102. The front leg straps 108, 110 may be used to form adjustable openings for front legs of an animal. For example, when brace 100 is worn, the front leg straps 108, 110 extend from the lower panel 104 near a chest portion of the animal. From there, the front leg straps 108, 110 may pass between the front legs of the animal and out in front of the animal. Then, the front leg straps 108, 110 may pass up from between the front legs of the animal over the animal's shoulders (on each side of its neck) to the animal's back. The front leg straps 108, 110 may be secured with the upper panel 102 on the animal's back to form adjustable loops for the front legs of the animal. It is to be appreciated that the front leg straps 108, 110 may wrap around the animal in other configurations to secure the front legs of the animal. For example, the front leg straps 108 may be "crisscrossed" over the animal's chest and neck to form openings for the front legs.

In a similar fashion, the rear leg straps 112, 114 may be used to form adjustable openings for rear legs of the animal. The rear leg straps 112, 114 extend from the upper panel 102 and down along respective sides of an animal to its lower abdomen (in front of the rear legs) when the brace 100 is worn. The rear leg straps 112, 114 pass along the lower abdomen of the animal, between the rear legs of the animal, and out behind the animal. From there, the rear leg straps 112, 114 pass over the hips of the animal (on each side of its tail) to the animal's back. The rear leg straps 112, 114 may be secured with the upper panel 102 on the animal's back to form adjustable loops for the rear legs of the animal. The rear leg straps 112, 114 may also be wrapped around the animal in various other configurations to secure the rear legs of the animal (e.g., the rear leg straps may be "crisscrossed" over the animal's lower abdomen). Although brace 100 is shown with leg straps, the brace may also be configured without front leg straps 108, 110 and without rear leg straps 112, 114. Alternatively, brace 100 may be configured with just front leg straps 108, 110 or just rear leg straps 112, 114.

One of the challenges attendant with designing a brace for supporting an animal's spine is to make the brace both supportive of the animal's spine and comfortable for the animal to wear. As previously described, introducing any additional discomfort for an animal such as a pet is undesirable, especially when the animal is already ailed by a ruptured or herniated disc. Conventional approaches to animal spine brace construction often called for using stiff materials. Although such braces support an animal's spine, using stiff materials also caused discomfort for the animal. Brace 100, however, may be made from a material that is form fitting and comfortable for an animal (e.g., a material that is breathable and lightweight).

As one example, brace 100 may be made from a material having a breathable open-cell polyurethane construction. Having an open-cell construction enables the material to wick moisture from an animal, which can help keep the animal cool and comfortable. The material may also be treated to control bacteria that cause perspiration odors. For example, the material may be laminated and silver nano-crystals may be physically bonded to the surface of the laminated material. A high concentration of silver present on the fabric may thus be used to reduce and even prevent an ability of bacteria to penetrate the fabric.

Additionally, the material from which brace 100 is made may be capable of four-way stretch (i.e., the ability to stretch both longitudinally and latitudinally as contrasted with two-way stretch material which typically only stretches from one selvedge of the material to another) and recovery from the stretch, such that the material provides at least some compression. Further, the material may also be latex free thereby eliminating most skin irritations.

Another challenge with designing a brace for supporting an animal's spine is to make the brace easy to put on and to take off of the animal. Difficulties with putting a brace on an animal may, for instance, cause further discomfort for the animal. Some conventional approaches to animal spine brace construction have resulted in braces that are difficult to put on an animal and thus cause the animal discomfort (e.g., a sleeve construction with which the animal's head and front legs have to be pulled through the sleeve). However, the illustrated brace 100 is configured with an "open" design to reduce difficulties attendant with putting the brace on an animal.

In one or more implementations, brace 100 may be configured with a series of releasable closures (e.g., hook-and-loop closures, buttons, magnets, zippers and the like) and expandable bands that enable the upper panel 102 and the lower panel 104 to be secured around an animal. For example, lower panel 104 extends from the upper panel 102 to wrap around the animal in a direction that is substantially perpendicular to the animal's spine. In this example, the upper panel 102 and lower panel 104 may be wrapped around the animal between its front and rear legs. To form an adjustable "sleeve" around the animal, the lower panel 104 may be releasably secured to the upper panel 102, such as with corresponding releasable closures 116, 118. Further, brace 100 may be configured with an expandable band 120 that wraps around the abdomen of the animal for further support. Alternatively, brace 100 may be configured without expandable band 120.

The front leg straps 108, 110 and rear leg straps 112, 114 may also be secured around the animal using releasable closures. As illustrated, the front leg straps 108, 110 include respective releasable closures 122, 124 that are positioned substantially near the end of the front leg straps. As discussed previously, the front leg straps 108, 110 may form loops around the front legs of the animal. In some implementations, respective releasable closures 122, 124 may be secured directly to the upper panel 102 when brace 100 is worn. Alternatively, respective releasable closures 122, 124 may be secured to corresponding closures disposed on the upper panel 102 (not shown). In the illustrated example, brace 100 also includes front leg strap security loops 126, 128. When brace 100 is worn, the front leg straps 108, 110 may, for example, pass through the front leg strap security loops 126, 128, an example of which may be seen in FIGS. 3C and 4.

Figure 3C:
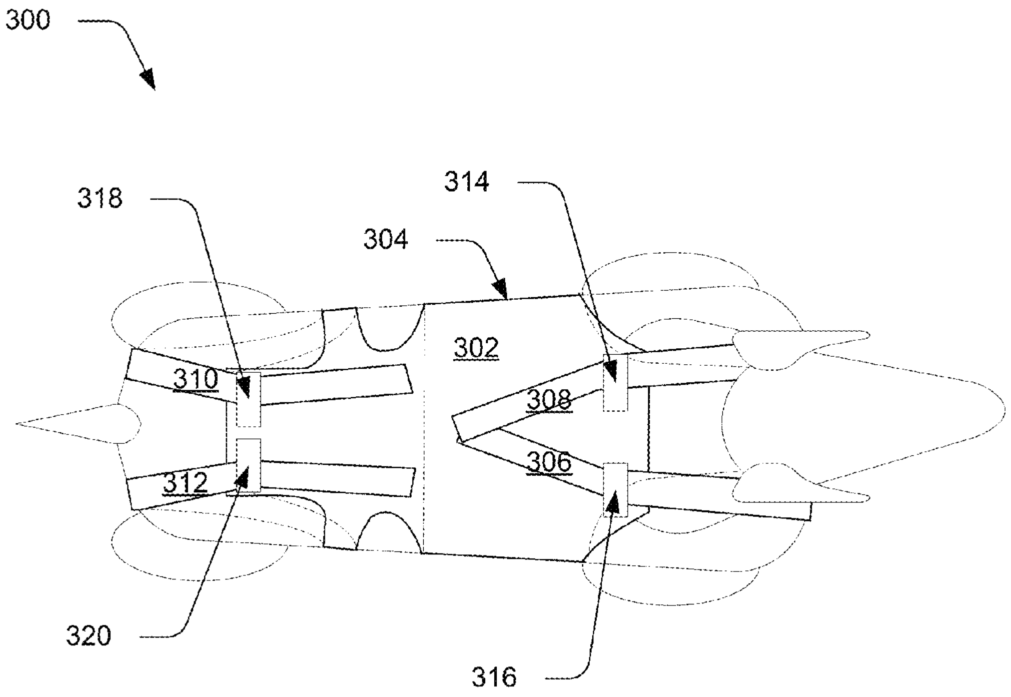
FIG. 3C is an illustration of the brace in an example implementation in which the brace is wrapped around the animal as in FIG. 3B, and in which leg straps that extend from upper and lower panels of the brace are wrapped around front and rear legs of the animal forming adjustable loops for the front and rear legs.
Figure 4:
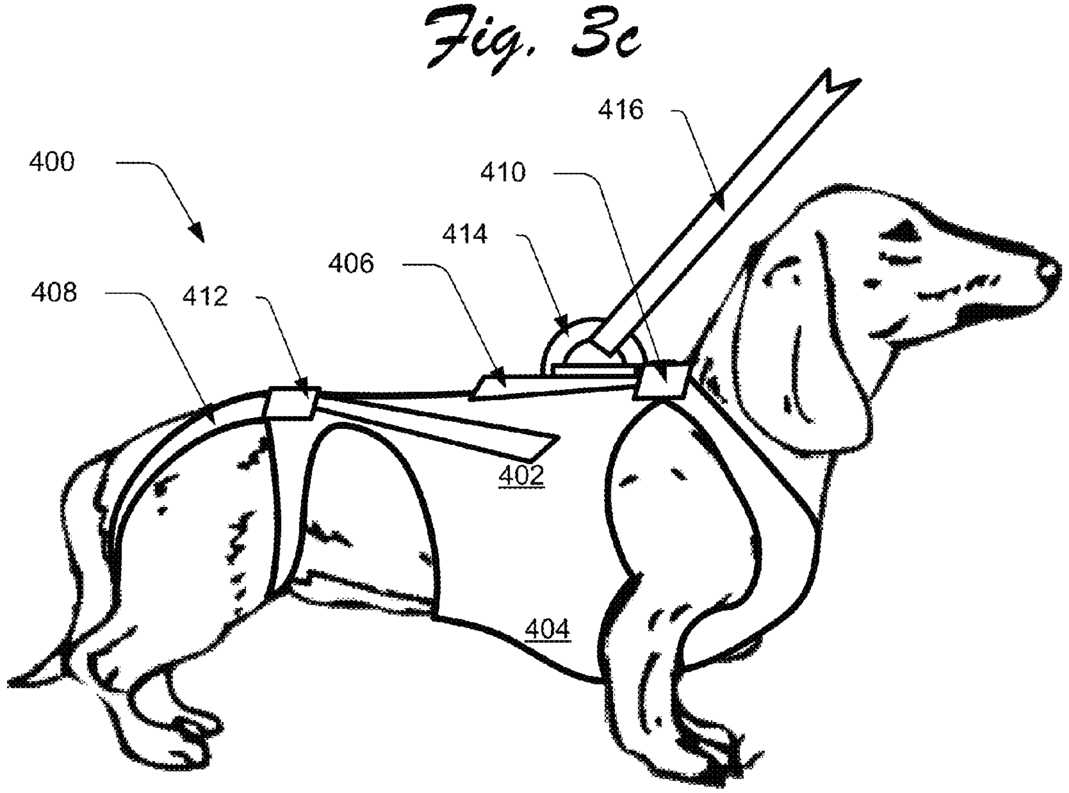
FIG. 4 is an illustration of a brace in an example implementation depicting an animal from a right side view wearing the brace.

Rear leg straps 112, 114 may also be secured around the animal using releasable closures. As shown in FIG. 1, rear leg straps 112, 114 include respective releasable closures 130, 132, which may be positioned at the end of the rear leg straps 112, 114. When the brace is worn, the rear leg straps 112, 114 may form loops around the rear legs of the animal and, the respective releasable closures 130, 132 may be used to secure the rear leg straps directly to the upper panel 102. The respective releasable closures 130, 132 may also be secured to corresponding closures disposed on the upper panel 102 (not shown). Further, brace 100 may include rear leg strap security loops 134, 136 through which the rear leg straps 112, 114 may be passed, as shown in FIGS. 3C and 4.

In addition to being configurable as a supportive "sleeve", brace 100 may be configured with "stays" that provide additional support for an animal's spine and abdomen. In conventional approaches to animal spine brace construction, supportive stays are typically disposed along a portion of the brace configured to cover an animal's back. Further, such supportive stays are also generally arranged in parallel, one to another.

However, brace 100 includes supportive stays 138, 140, 142, 144, 146 that are disposed on the upper panel 102 (supporting a spine and back of an animal) as well as supportive stays 148, 150, 152 that are disposed on the lower panel 104 (supporting a chest and abdomen of the animal). In this example, supportive stays 138, 140, 142, 144, 146 are arranged on the upper panel 102 to fan outwardly from longitudinal axis 154 (which is substantially parallel to an animal's spine when the brace is worn). The supportive stays 148, 150, and 152, which are disposed on the lower panel 104 are also arranged to fan outwardly from a longitudinal axis.

Figure 2:
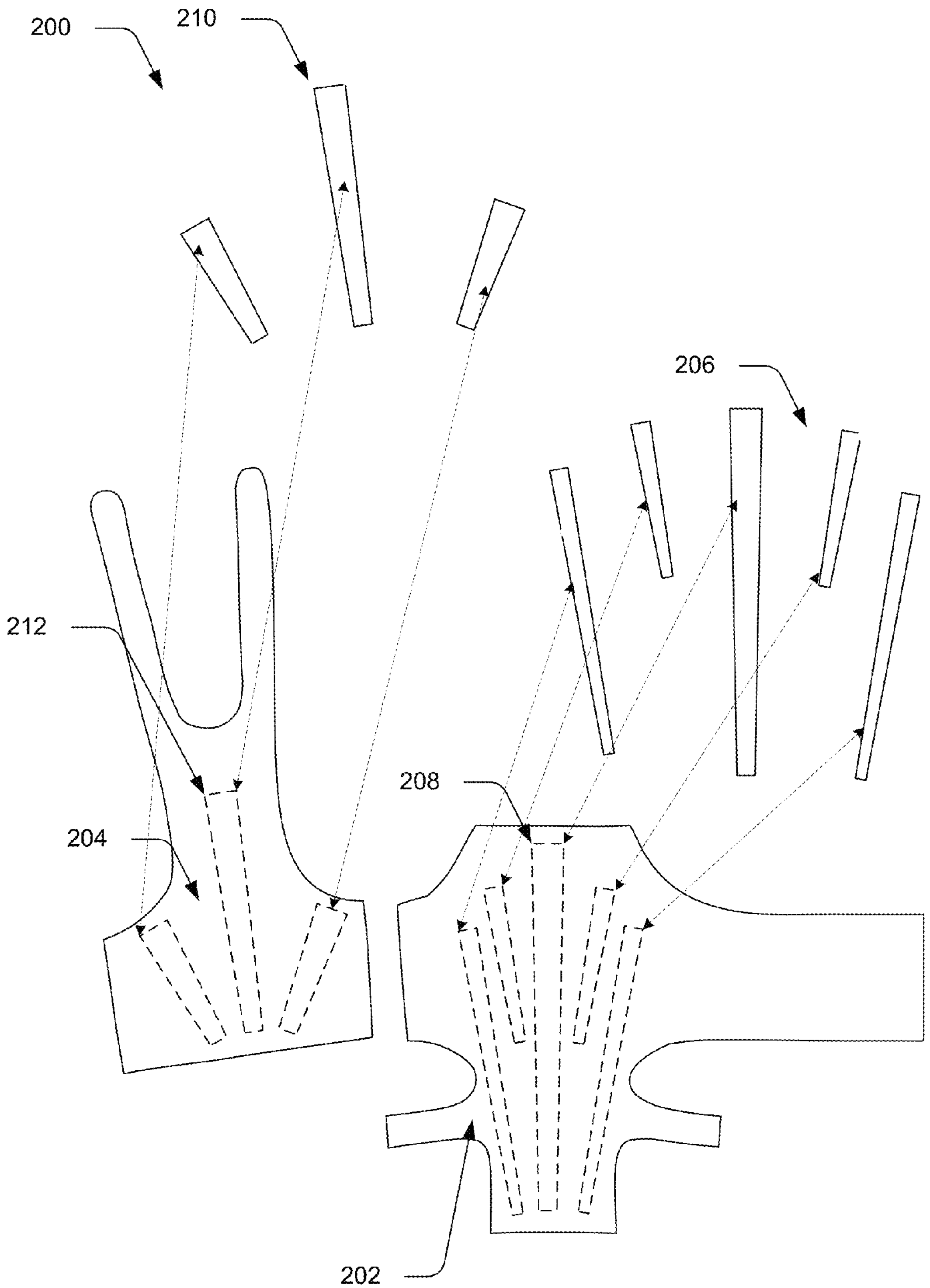
FIG. 2 is an illustration of a brace in an example implementation showing an arrangement of supportive stays on an upper panel and a lower panel of the brace.

FIG. 2 is an illustration of a brace 200 in an example implementation showing an arrangement of supportive stays on an upper panel and a lower panel of the brace. The upper panel 202 and the lower panel 204 may correspond to upper panel 102 and lower panel 104 of FIG. 1 respectively. Multiple supportive stays 206 may be arranged on the upper panel 202 to fan outwardly from a longitudinal axis (i.e., an axis that is substantially parallel to an animal's spine when the brace is worn). For example, the multiple supportive stays 206 may be arranged in positions 208. In this example, the supportive stays that are disposed nearest to the longitudinal axis are substantially parallel. It should be appreciated that the multiple supportive stays 206 may be integrated on top of, within, or along an underside of the upper panel 202.

In one or more implementations, each of the multiple supportive stays 206 may be arranged relative to a respective longitudinal axis. When brace 200 is worn by an animal, the longitudinal axis corresponding to a particular supportive stay runs through a first point of the supportive stay nearer to the animal's tail and a second point of the supportive stay that is further from the tail than the first point. The multiple supportive stays 206 may be configured to fan out from the tail such that a distance between the first point of two supportive stays is shorter than a distance between the second point of the two supportive stays.

Additional supportive stays 210 may be arranged on the lower panel 204 to support an abdomen and chest of an animal. These additional supportive stays 210 may be arranged to fan outwardly relative to a different longitudinal axis (i.e., an axis that runs along the abdomen of an animal and is substantially parallel to the animal's spine when the brace is worn). For example, the additional supportive stays 210 may be arranged in positions 212 and integrated on top of, within, or along an underside of the lower panel 204. In this example, the supportive stays that are disposed nearest to the different longitudinal axis are substantially parallel to the different longitudinal axis.

In one or more implementations, the multiple supportive stays 206 and the additional supportive stays 210 are made from a material that is configured to be substantially rigid, such as hard plastic, metal, heavy leather, and so on. However, the supportive stays may be made of any substance that enables the stays to provide support for an animal's spine and abdomen. Additionally, the supportive stays may be removable from the respective upper and lower panels such that brace 200 can be worn with some of the supportive stays, or alternatively, without any supportive stays.

Figure 3A:
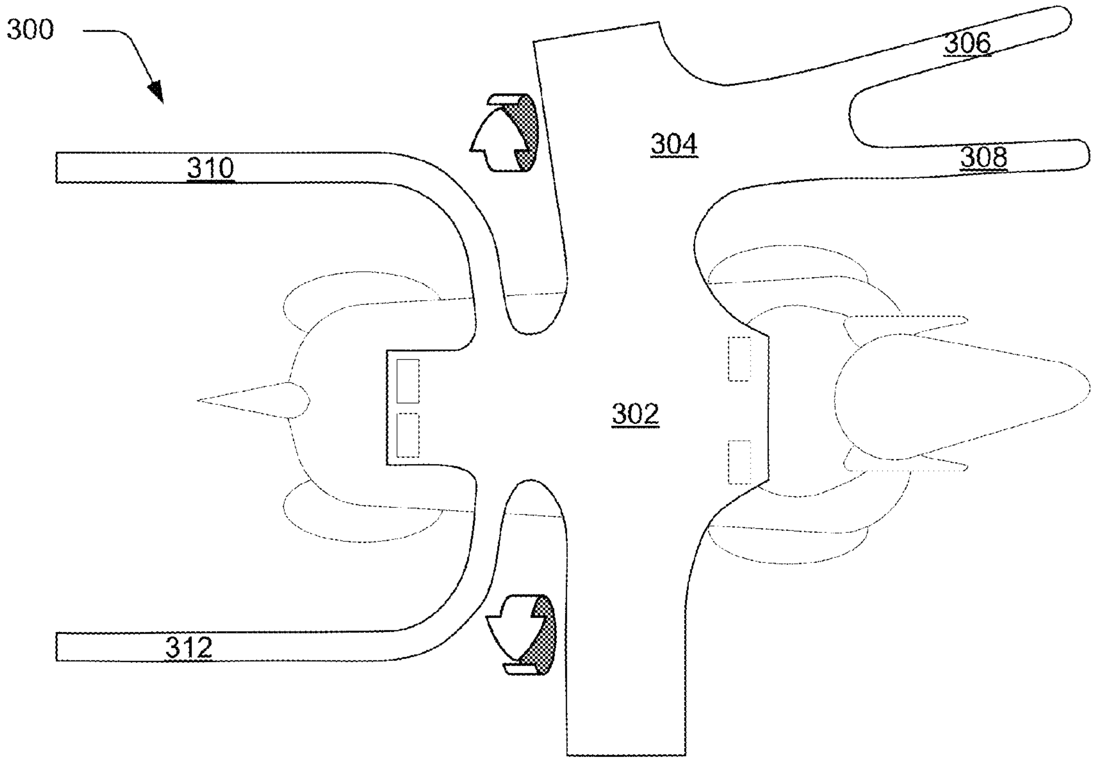
FIG. 3A is an illustration of a brace in an example implementation depicting an animal and the brace (from above), which may be configured in accordance with one or more of the previously described braces of FIGS. 1 and 2.

FIG. 3A is an illustration of a brace 300 in an example implementation depicting an animal and the brace (from above), which may be configured in accordance with one or more of the previously described braces of FIGS. 1 and 2. In this example, brace 300 is shown in the "open" position and is positioned directly above a dog.

When brace 300 is in the "open" position, the upper and lower panels 302, 304 are not wrapped around the dog to form an adjustable sleeve. As shown, front leg straps 306, 308 extend from the lower panel 304 and are not wrapped around dog. Further, rear leg straps 310, 312 are shown extended from the upper panel 302 and are not wrapped around the dog.

Figure 3B:
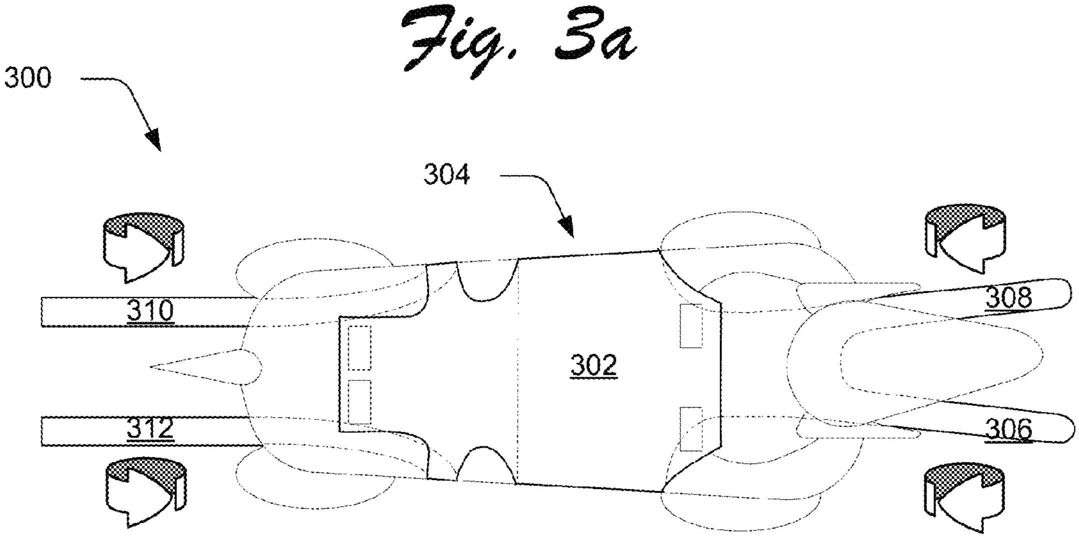
FIG. 3B is an illustration of the brace in an example implementation in which the brace is wrapped around the animal forming an adjustable sleeve.

FIG. 3B is an illustration of the brace 300 in an example implementation in which the brace is wrapped around the animal forming an adjustable sleeve. In this example, the upper panel 302 and the lower panel 304 have been wrapped around the dog in a direction that is substantially perpendicular to the dog's spine. In particular, the upper panel 302 and the lower panel 304 are shown wrapped around the dog between its front and rear legs, forming a sleeve around the dog's midsection. The lower panel 304 may be releasably secured to the upper panel 302, enabling the "sleeve" to be adjustable.

As shown in FIG. 3B, the front leg straps 306, 308 extend from a portion of the lower panel 304 that is positioned substantially near the chest of the dog and extend out between the dog's front legs. In this illustration, the rear leg straps 310, 312 are shown wrapped down the sides of the dog, under its lower abdomen, and extending out between its rear legs.

FIG. 3C is an illustration of the brace 300 in an example implementation in which the brace is wrapped around the animal as in FIG. 3B. In this figure, leg straps that extend from upper and lower panels of the brace are wrapped around front and rear legs of the animal forming adjustable loops for the front and rear legs. As illustrated, the front leg straps 306, 308 are wrapped over the shoulders of the dog. The front leg straps 306, 308 are shown passing through front leg strap security loops 314, 316, which may be used to secure the front leg straps and to form adjustable loops for the dog's front legs. Further, the rear leg straps 310, 312 are shown passing through rear leg strap security loops 318, 320. The rear leg strap security loops 318, 320 may be used to secure the rear leg straps 310, 312 and to form adjustable loops for the dog's rear legs. Additionally or in the alternative, front leg straps 306, 308 and rear leg straps 310, 312 may be releasably secured to the upper panel 302 to form the adjustable leg loops without passing through leg strap security loops.

FIG. 4 is an illustration of a brace 400 in an example implementation depicting an animal from a right side view wearing the brace. An upper panel 402 and a lower panel 404 of brace 400 are shown wrapped around a dog, such that the brace forms a sleeve around the dog. In this example, a front right leg strap 406 is shown wrapped around the front right leg of the dog and secured to the upper panel 402 of brace 400. Similarly, a rear right leg strap 408 is shown wrapped around the rear right leg of the dog and secured to the upper panel 402 of brace 400. Both the front right leg strap 406 and the rear right leg strap 408 are shown passing through respective leg strap security loops 410, 412.

As shown in FIG. 4, brace 400 may optionally include an attachment for a leash. In this example, D-ring 414 is shown disposed on upper panel 402 substantially behind a neckline and between shoulders of the dog. D-ring 414 is configured to secure leash 416 with brace 400. Although D-ring 414 is positioned behind the neckline and between the shoulders of the dog in this example, this exemplary placement should not be seen to limit the placement of the D-ring. For instance, D-ring 414 may be integrated with other portions of brace 400, such as with upper panel 402 nearer to a tail of the dog or integrated with lower panel 404. Further, leash 416 may be secured to brace 400 using other attachments that are configured to secure the leash to the brace (e.g., a loop of breathable material, webbing, a chain, and so on). Additionally, the leash attachment may be removable from brace 400, such that the brace may be worn with or without the attachment. In yet another example, the leash attachment may be movable, such that the attachment may be secured to brace 400 at multiple different locations on the brace.

CONCLUSION

Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

What is claimed is:

1. A brace comprising:

a breathable upper panel configured to cover a back and upper side portions of an animal;

a breathable lower panel, which extends from the breathable upper panel, and is configured to cover an abdomen and lower side portions of the animal;

rear leg straps that extend from the breathable upper panel, the rear leg straps configured to be releasably secured to the breathable upper panel to form adjustable loops around rear legs of the animal; and front leg straps that extend from the breathable lower panel, the front leg straps configured to be releasably secured to the breathable upper panel to form adjustable loops around front legs of the animal.

2. A brace as described in claim 1, wherein the breathable upper panel and the breathable lower panel comprise breathable material that is configured to stretch longitudinally and latitudinally.

3. A brace as described in claim 1, wherein the breathable upper panel and the breathable lower panel comprise breathable material that is configured to wick moisture from the animal.

4. A brace as described in claim 1, wherein the breathable upper panel and the breathable lower panel comprise breathable material that is configured to control perspiration odors.

5. A brace as described in claim 1, wherein the breathable lower panel extends from the breathable upper panel to wrap around the animal in a direction that is substantially perpendicular to a spine of the animal.

6. A brace as described in claim 1, wherein the breathable lower panel extends from the breathable upper panel to wrap around the animal between front and rear legs of the animal.

7. A brace as described in claim 1, wherein the breathable lower panel is configured to be releasably secured to the breathable upper panel to form a sleeve around the animal that is adjustable.

8. A brace as described in claim 1, wherein the rear leg straps are configured to be releasably secured to the breathable upper panel to form the adjustable loops around rear legs of the animal such that:

the rear leg straps pass underneath a lower abdomen portion of the animal between the rear legs; and the rear leg straps pass up from between the rear legs of the animal over respective hip portions of the animal to secure with the breathable upper panel.

9. A brace as described in claim 1, wherein the front leg straps are configured to be releasably secured to the breathable upper panel to form the adjustable loops around front legs of the animal such that:

the front leg straps pass underneath a chest portion of the animal between the front legs; and the front leg straps pass up from between the front legs of the animal over respective shoulder portions of the animal to secure with the breathable upper panel.

10. A brace as described in claim 1, further comprising a D-ring configured to secure a leash to the brace.

11. A brace comprising:

a wrap portion that is configured to form an adjustable sleeve around an animal;

a plurality of supportive stays that are integral with the wrap portion and configured to fan outwardly from a longitudinal axis that is substantially parallel to a spine of the animal, the plurality of supportive stays are:

each disposed relative to a respective longitudinal axis that runs through a first point of a supportive stay that is nearer to a tail portion of the animal and a second point of the supportive stay that is further from the tail than the first point; and configured to fan out such that a distance between the first point of the first and second said supportive stays is shorter than a distance between the second point of the first and second said supportive stays; and an additional plurality of supportive stays that are integral with a lower panel of the wrap portion that is configured to cover an abdomen and lower side portions of the animal.

12. A brace as described in claim 11, wherein one or more of the plurality of supportive stays nearest to the longitudinal axis are substantially parallel to the longitudinal axis.

13. A brace as described in claim 11, wherein the plurality of supportive stays are made of a material that is configured to be substantially rigid.

14. A brace as described in claim 11, wherein the plurality of supportive stays are integral with an upper panel of the wrap portion that is configured to cover a back and upper side portions of the animal.

15. A brace as described in claim 11, wherein the additional plurality of supportive stays are configured to fan outwardly from an additional longitudinal axis that runs along the abdomen of the animal and is substantially parallel to the spine of the animal.

16. A brace as described in claim 11, further comprising a D-ring disposed on the wrap portion of the brace and configured to secure a leash to the brace.

17. A brace comprising:

an upper panel that is configured to cover a back and upper side portions of an animal;

a lower panel that extends from the upper panel and includes a plurality of supportive stays, the lower panel configured to cover an abdomen and lower side portions of the animal and to be releasably secured to the upper panel to form a sleeve around the animal that is adjustable, the plurality of supportive stays are:

each disposed relative to a respective longitudinal axis that runs through a first point of a supportive stay that is nearer to a tail portion of the animal and a second point of the supportive stay that is further from the tail than the first point; and configured to fan out such that a distance between the first point of first and second said supportive stays is shorter than a distance between the second point of the first and second said supportive stays;

rear leg straps that extend from the upper panel, the rear leg straps configured to be releasably secured to the upper panel to form adjustable loops around rear legs of the animal; and front leg straps that extend from the lower panel, the front leg straps configured to be releasably secured to the upper panel to form additional adjustable loops around front legs of the animal.

18. A brace as described in claim 17, wherein the upper panel includes an additional plurality of supportive stays, wherein:

the plurality of supportive stays are configured to fan outwardly from a longitudinal axis that runs along the abdomen of the animal and is substantially parallel to a spine of the animal; and the additional plurality of supportive stays are configured to fan outwardly from an additional longitudinal axis that runs along the back of the animal and is substantially parallel to the spine of the animal.

19. A brace as described in claim 17, wherein the upper panel and the lower panel comprise breathable material configured to at least one of:

stretch longitudinally and latitudinally;

wick moisture from the animal; and control perspiration odors.

20. A brace as described in claim 17, further comprising a D-ring disposed on the upper panel of the brace, the D-ring configured to be positioned behind a neckline and between shoulders of the animal and to secure a leash to the brace.

* * * * *